(12) United States Patent
Dejeaifve et al.

(10) Patent No.: US 10,590,047 B2
(45) Date of Patent: *Mar. 17, 2020

(54) IONONE STABILISERS FOR NITROCELLULOSE-BASED PROPELLANTS

(71) Applicant: PB CLERMONT SA, Engis (BE)

(72) Inventors: Alain Dejeaifve, Engis (BE); Rowan Dobson, Engis (BE)

(73) Assignee: PB CLERMONT, Engis (BE)

( * ) Notice: Subject to any disclaimer, the term of this patent is extended or adjusted under 35 U.S.C. 154(b) by 232 days.

This patent is subject to a terminal disclaimer.

(21) Appl. No.: 15/552,635

(22) PCT Filed: Feb. 25, 2016

(86) PCT No.: PCT/EP2016/053946
§ 371 (c)(1),
(2) Date: Aug. 22, 2017

(87) PCT Pub. No.: WO2016/135227
PCT Pub. Date: Sep. 1, 2016

(65) Prior Publication Data
US 2018/0029951 A1    Feb. 1, 2018

(30) Foreign Application Priority Data

Feb. 25, 2015   (EP) .................................. 15156491

(51) Int. Cl.
*C06B 25/26* (2006.01)
*C06B 23/00* (2006.01)
(Continued)

(52) U.S. Cl.
CPC ............ *C06B 23/006* (2013.01); *C06B 25/20* (2013.01); *C06B 25/26* (2013.01); *C07C 39/07* (2013.01);
(Continued)

(58) Field of Classification Search
USPC .................... 149/88, 96, 98, 108.8
See application file for complete search history.

(56) References Cited

U.S. PATENT DOCUMENTS

2018/0029952 A1*   2/2018   Dejeaifve ............ C06B 23/006

OTHER PUBLICATIONS

Naves et al., Helv. Chim. Acta, 30, 419 (1947).*
(Continued)

*Primary Examiner* — James E McDonough
(74) *Attorney, Agent, or Firm* — Norris McLaughlin, P.A.

(57) ABSTRACT

The present disclosure is directed to a nitrocellulose-based propellant composition comprising: (a) a nitrate ester-based propellant comprising nitrocellulose; and (b) a stabiliser comprising a non-aromatic compound (12) consisting of a general ionone formula (12-I), (12-II), (12-III) or (12-IV):

(12-I)

(12-II)

(12-III)

(Continued)

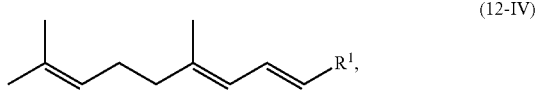

(12-IV)

wherein $R^1$ represents a ketone, hydroxyl, carboxyl, aldehyde or an unsaturated alkyl group, preferably —C(O)CH$_3$ (corresponding to alpha, beta, gamma and pseudo ionone).

14 Claims, 8 Drawing Sheets (51) Int. Cl.
| | |
|---|---|
| C06B 25/20 | (2006.01) |
| C07C 39/07 | (2006.01) |
| C07C 43/23 | (2006.01) |
| C07C 49/21 | (2006.01) |
| C06B 25/00 | (2006.01) |
| C06B 25/18 | (2006.01) |
| D03D 23/00 | (2006.01) |
| D03D 43/00 | (2006.01) |

(52) U.S. Cl.
CPC .............. *C07C 43/23* (2013.01); *C07C 49/21* (2013.01); *C07C 2601/16* (2017.05)

(56) References Cited

OTHER PUBLICATIONS

Wilker, Stephan, et al., "Stability Analysis of Propellants Containing New Stabilizers—part IV: are phenols a possible alternative to aromatic amines?", Fraunhofer-Institut fuer Chemische Technologie, Apr. 26, 2007, Swisttal, Germany.

Harrison, J.C., et al., "[beta] Ionone Reactions With the Nitrate Radical: Rate Constant and Gas-phase Products", International Journal of Chemical Kinetics, Oct. 2009, pp. 629-641, vol. 41 No. 10, John Wiley and Sons Inc., United States of America.

Forester, et al., "beta-Ionone Reactions With Ozone and OH Radical: Rate Constants and Gas-phase Products", Atmospheric Environment, Nov. 26, 2007, pp. 8758-8771, vol. 41, No. 38, Pergamon, Great Britain.

Chin, Anton, et al., "Investigation of the decomposition Mechanism and Thermal Stability of Nitrocellulose/Nitroglycerine Based Propellants by Electron Spin Resonance", Wiley InterScience, Propellants, Explosives, Pyrotechnics, Apr. 1, 2007, pp. 117-126, vol. 32, No. 2; Wiley-VCH Verlag GmbH & Co., KGaA, Weinheim, Germany.

NATO Standarization Agency, "Explosives, nitrocellulose-based propellants, stability test procedure and requirements using heat flow calorimetry", 24 pages, STANAG 4582, Ed. 1, North Atlantic Treaty Organisation, Brussels, Belgium.

Venter, Andre., et al., "A Desorption Electrospray Ionization Mass Spectrometry Study of Aging Products of Diphenylamine Stabilizer in Double-base Propellants", Propellants, Esplosives, Pyrotechnics, Dec. 1, 2006, pp. 472-476, vol. 31, No. 6, Wiley-VCH Verlag GmbH & Co., Weinheim, Germany.

International Search Report for corresponding PCT Application No. PCT/EP2016/053946 dated Apr. 4, 2016.

International Preliminary Report on Patentability and Written Opinion of the International Searching Authority for corresponding PCT Application No. PCT/EP2016/053946 dated Apr. 4, 2016.

* cited by examiner

IONONE STABILISERS FOR NITROCELLULOSE-BASED PROPELLANTS

This application is a 371 application of PCT/EP2016/053946 filed 25 Feb. 2016, which claims foreign priority benefit under 35 U.S.C. § 119 of European application 15156491.1 filed 25 Feb. 2015.

TECHNICAL FIELD

The present invention relates to stabilised nitrocellulose-based propellant compositions. In particular it concerns nitrocellulose-based propellant stabilised with a stabiliser producing little to no carcinogenic and mutagenic by-products.

BACKGROUND FOR THE INVENTION

Smokeless powders have been developed since the 19th century to replace traditional black powder, which generates substantial amounts of smoke when fired. The most widely used smokeless powders are nitrocellulose-based. Nitrocellulose is obtained by using nitric acid to convert cellulose into cellulose nitrate and water according to a general reaction:

$$3HNO_3 + C_6H_{10}O_5 \rightarrow C_6H_{17}(NO_2)_3O_5 + 3H_2O$$

Nitrocellulose-based smokeless powder is then obtained by treating the thus obtained nitrocellulose by extrusion or spherical granulation, with or without solvent, two techniques which are well known to the persons skilled in the art.

Various improvements have been developed since the first discovery of nitrocellulose, by addition of further components, such as nitroglycerine and/or nitroguanidine allowing an increase of the detonation velocity. Pure nitrocellulose propellant is referred to as single-base propellant, and double- and triple-base propellants refer to compositions comprising nitrocellulose and one or two additional energetic bases, respectively, typically blasting oils such as nitroglycerine, nitroguanidine, or secondary explosives.

Nitrocellulose, as most nitrate esters, is prone to self-ignition as a result of thermal degradation due to the weakness of its O—N bond. When employed as an ingredient of propellants or other explosive compositions, the spontaneous ignition of nitrocellulose has caused serious accidents. It is obviously vital to inhibit or slow down this degradation for safety reasons but it is also important to retain the initial properties of the energetic composition. Degradation usually leads to gas emissions, heat generation and reduction of molecular mass affecting negatively the material structure and ballistic properties.

Figure 1:
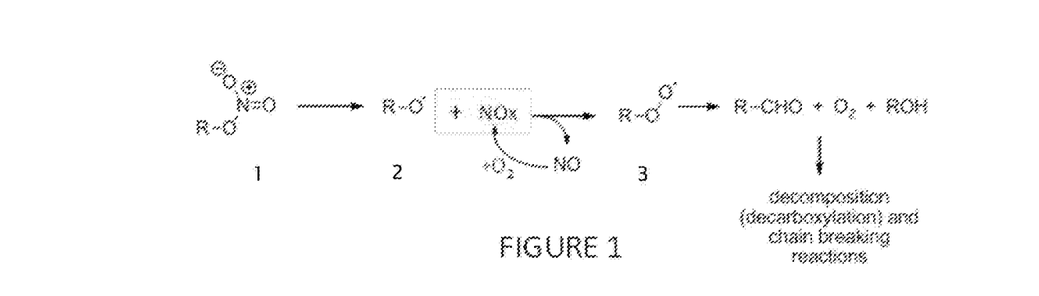
FIG. 1 shows a reaction of spontaneous decomposition of nitrocellulose with formation of free radicals and NOx.

The decomposition of nitrocellulose usually starts with a bond scission or hydrolysis, generating alkoxy radicals and nitrogen oxide (NOx) species (cf. FIG. 1). The radicals further react, generating more radicals, speeding up the degradation process, and ultimately lead to chain scission accompanied by heat generation. In order to prolong the service life of the propellants, stabilisers are added to the energetic mixture in order to scavenge these radical species and slow down the degradation pattern.

Figure 2A:
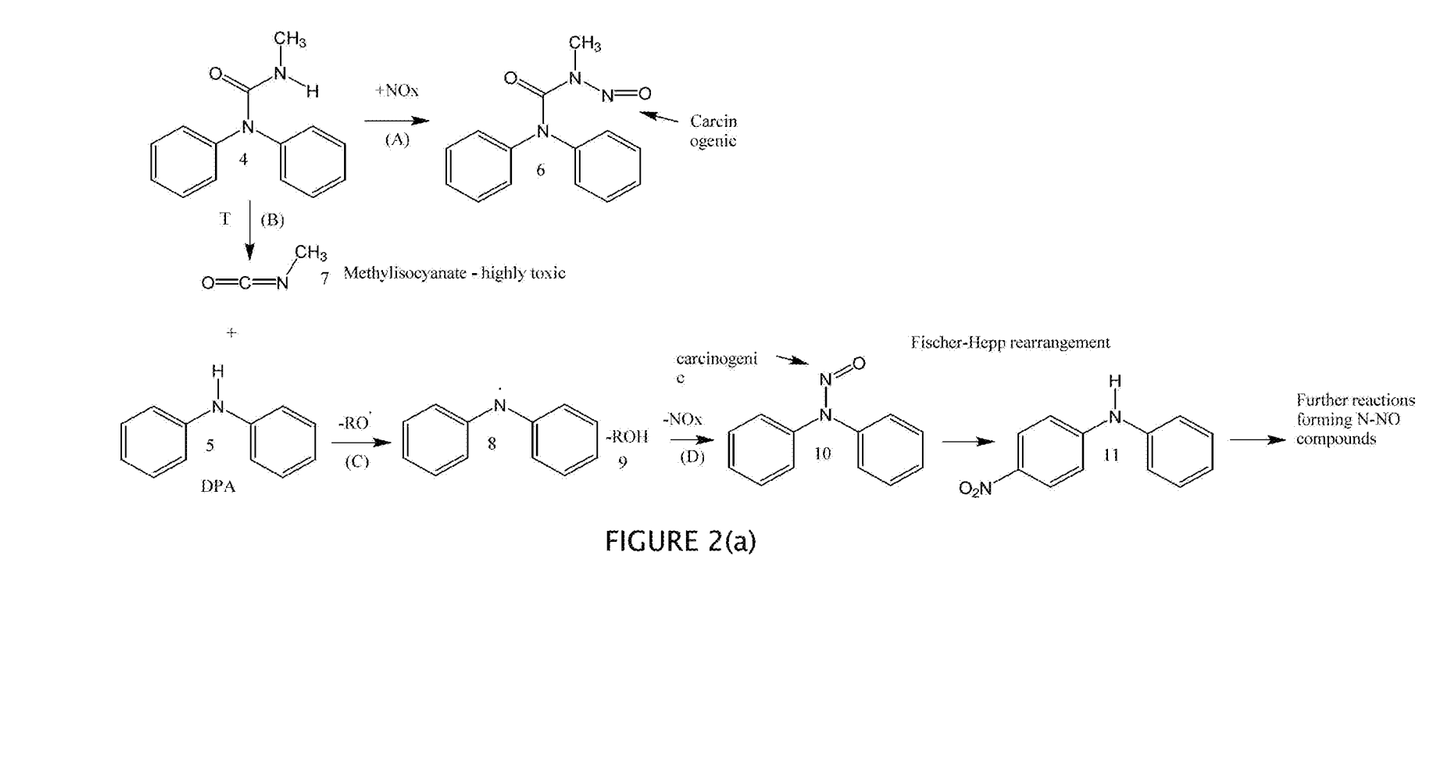
FIG. 2 shows assumed stabilisation mechanisms of akardite (AkII) and diphenylamine (DPA) (prior art).

All conventional stabilisers used to date for nitrocellulose-based propellants belong to (a) aromatic amines (e.g., diphenylamine, 4-nitro-N-methylamine) or (b) aromatic urea derivatives (e.g., akardite, centralite) and are or produce toxic and/or potentially carcinogenic species at some point during the propellant's lifetime. For example, the most widely used stabilisers to date are diphenylamine, akardite, and centralite. These compounds, however, form carcinogenic derivatives such as N-nitrosodiphenylamine (cf. FIG. 2(a)) or N-nitrosoethylphenylamine.

Figure 2B:
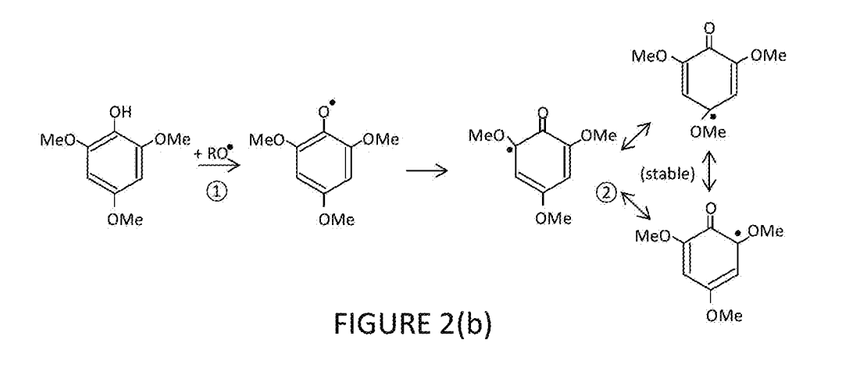

Hindered amines, such as triphenylamine, reduce the formation of N—NO groups, but fail to stabilise nitrocellulose satisfactorily. Conventional hindered phenols used in the plastics industry have been tested and at short term stabilise nitrocellulose with little to no N—NO formation. The phenols are able to trap the alkoxy radicals generated during the degradation of nitrocellulose and thus form new, relatively stable alkoxy radicals, by delocalisation of an electron at the foot of electron-rich, hindered groups as illustrated in FIG. 2(b). Long term stability is, however, not always guaranteed, probably due to rapid phenol depletion and relative stability of the newly formed alkoxy radicals.

There thus remains in the field of solid propellants a need for stabilisers allowing long term stabilisation of nitrocellulose based propellants, fulfilling at least STANAG 4582 (Ed.1) and which do not produce carcinogenic and/or mutagenic by-products. The present invention proposes a family of stabilisers fulfilling both requirements above. These and other advantages of the present invention are presented in continuation.

SUMMARY OF THE INVENTION

The present invention is defined in the appended independent claims. Preferred embodiments are defined in the dependent claims. In particular, the present invention concerns a nitrocellulose-based propellant composition comprising:

(a) a nitrate ester-based propellant comprising nitrocellulose; and

(b) a stabiliser consisting of a non-aromatic, ionone-type compound with a general formula (12-I), (12-II), (12-III) or (12-IV):

(12-I)

(12-II)

(12-III)

(12-IV)

wherein $R^1$ represents a ketone, hydroxyl, carboxyl, aldehyde or (un)saturated alkyl group.

The nitrate ester-based propellant may be a single base propellant consisting of nitrocellulose alone or, alternatively, may be a double or higher base propellant comprising nitrocellulose in combination with at least one blasting oil and/or at least one energetic additive. As known by a person skilled in the art, a blasting oil is herein defined as an energetic compound obtained by nitration of a polyol such as glycerol, glycol, diethylene glycol, triethylene glycol, metriol. The obtained nitrate is most of the time heavy, oily and presents explosive properties. Nitroglycerine is probably the most common blasting oil employed in the industry. The term "NOx" is used herein in its generally recognised sense, as a generic term for mono-nitrogen oxides NO and $NO_2$ (nitric oxide and nitrogen dioxide). In a preferred embodiment, the blasting oil comprises at least a nitrated polyol, said nitrated polyol is obtained by nitration of polyol selected from a group consisting of glycerol, glycol, diethylene glycol, triethylene glycol and metriol, preferably glycerol.

An energetic additive according to the present invention; like blasting oils, are used to enhance the blasting power of nitrocellulose. Energetic additives can be an energetic plasticiser or an explosive. Examples of energetic plasticisers comprise nitramines, such as butyl-NENA or dinitrodiazaalkane (DNDA). Examples of explosives suitable for use as energetic additives include RDX, HMX, FOX7, FOX12, CL20.

The preferred stabilisers of the present invention are capable of reacting with both degradation products of the nitrate ester: alkoxy radicals and NOx. Firstly, by hydrogen abstraction of the labile proton of the stabiliser, by reaction with a radical group, thus forming a stable alcohol compound and a first by-product able to trap further alkoxy/NOx species. The thus formed successive by-products are capable of reacting with NOx and alkoxy radicals from the degradation of the nitrate ester. No harmful NNO groups are formed due to the lack of nitrogen atoms in the stabiliser structure.

It is preferred that the blasting oil comprises at least a nitrated polyol, said nitrated polyol is obtained by nitration of polyol selected from a group consisting of glycerol, glycol, diethylene glycol, triethylene glycol and metriol, preferably glycerol.

The stabiliser of formula (12-I) is preferably alpha ionone, wherein $R^1$ is —C(O)CH$_3$:

(12-Ia)

The $R_1$ group for the non-aromatic compound of formula 12-(IV) is preferably a methyl aldehyde, corresponding to pseudo-ionone:

(12-IVa)

The $R^1$ group for stabiliser of formula (12-II) is preferably:

wherein $R^2$ represents CH$_2$OH, —CHO, or, —CH$_2$OC(=O) $R^3$, $R^3$ represents alkyl group substituted or not. In a preferred embodiment, the stabiliser corresponds to retinyl palmitate:

(12-IIa)

Unless otherwise specified, the expression "substituted or not" is to be construed as any —H in a molecule may be substituted by any of an alkyl, alkene, or an aromatic ring. A propellant composition is considered as being a "nitrocellulose-based propellant composition" if it comprises at least 40 wt. % nitrocellulose, based on the total weight of the composition.

The stabiliser may be present in the composition in an amount comprised between 0.1 and 5.0 wt. %, preferably between 0.2 and 2.0 wt. %, more preferably between 0.5 and 1.5 wt. %, with respect to the total weight of the composition. The nitrate ester-based propellant may comprise nitrocellulose only, thus defining a single base propellant or, alternatively, it may comprise a blasting oil, such as nitroglycerine, to define a double base propellant. A double base propellant according to the present invention preferably comprises not more than 60 wt. % nitroglycerine, and preferably comprises between 5 and 45 wt. %, more preferably between 7 and 22 wt. % nitroglycerine, with respect of the total weight of nitrate ester based propellant.

The propellant compositions of the present invention should fulfil the stability requirements defined in STANAG 4582 (Ed.1), namely generating less than 350 μW/g of heat flow for at least 3.43 days at a temperature of 90° C. Many propellant compositions of the present invention can achieve much better than this and may remain stable for over 10 days at 90° C.

The composition of the present invention may further comprise an aromatic compound as complementary stabiliser. In particular, said complementary stabiliser may comprise one of the following compounds:

(a) a substituted phenol compound (13) having the general formula (13-I):

(13-I)

wherein: $R^3$ represents: (i) H, (ii) alkyl substituted or not, or (iii) an alkoxy group; and $R^4$ and $R^5$ are same or different, and represent (i) alkyl substituted or not, or (ii) alkoxy group;

(b) a trialkoxy benzene (14) having the general formulae (14-I) or (14-II):

wherein $R^6$, $R^7$ and $R^8$ are same or different and represent $C_{1-5}$ alkyl unsubstituted or substituted with an alkoxy group; or (c) an aromatic compound (15) having a general formula (15-I):

Wherein: $R^9$ represents, alkyl substituted or not; $R^{10}$ represent (i) H, (ii) unsaturated alkyl group,

$R^{11}$ represents, H, alkyl substituted or not, or $OR^{15}$;
$R^{12}$ represents, alkyl substituted or not, aromatic ring substituted or not, or $OR^{15}$;
$R^{13}$ represents, alkyl substituted or not, aromatic ring substituted or not, or $OR^{16}$;
$R^{14}$ represents, aromatic ring substituted or not;
$R^{15}$ represents, alkyl substituted or not, or aromatic ring substituted;
$R^{16}$ represents, alkyl substituted or not, or aromatic ring substituted (d) a substituted phenol compound (16) having the general formula (16-I):

wherein: $R^{20}$, $R^{21}$ and $R^{22}$ are the same or different and represent: (i) alkyl-substituted or not, (ii) alkoxy group.

(e) a substituted phenol compound (17) having the general formula (17-I):

wherein: $R^{23}$, $R^{24}$, $R^{25}$ and $R^{26}$ are the same or different and represent: (i) alkyl-substituted or not, (ii) alkoxy group.

(f) A tocopherol-class compound (18) with the general formula (18-I):

wherein:
X is oxygen or nitrogen;
$R^{27}$ is selected from the group consisting of hydrogen, alkyl, alkenyl, alkynyl, aryl, heteroaryl, carboxylic acid, carboxylate, ester, saccharide, alkoxy-linked saccharide, alcohol, and ether;
$R^{28}$ is selected from the group consisting of hydrogen methyl, benzyl carboxylic acid, benzyl carboxylate, benzylester, and saccharide;
$R^{29}$ is selected from the group consisting of hydrogen, methyl, benzyl carboxylic acid, benzyl carboxylate, benzylester and, saccharide;
$R^{30}$ is selected from the group consisting of methyl, benzyl carboxylic acid, benzyl carboxylate, benzylester, and saccharide;

$R^{31}$ is selected from the group consisting of alkyl and alkenyl;

Wherein when X is nitrogen, said nitrogen is substituted with $R^{32}$, wherein $R^{32}$ is selected from the group consisting of hydrogen and methyl.

Beside a nitrate ester based propellant and a stabiliser, the propellant compositions of the present invention may comprise additives. In particular, they may comprise one or more of the following additives:

(a) a potassium salt, such as potassium nitrate ($KNO_3$) or sulphate ($K_2SO_4$), preferably in an amount comprised between 0.01 and 1.5 wt. %;
(b) combustion moderators such as phthalates, Cl and citrate derivatives, preferably in an amount comprised between 1.0 and 10.0 wt. %;
(c) an anti-static agent such as graphite, preferably in an amount comprised between 0.01 and 0.5 wt. %; and
(d) calcium carbonate, preferably in an amount comprised between 0.01 and 0.7 wt. %, Wherein the wt. % are expressed in terms of the total weight of the propellant composition.

The present invention also concerns the use of a stabiliser of formula (12-I) to (12-IV) as defined above, for stabilising a nitrocellulose based propellant composition. The stabiliser is preferably of a formula (12-Ia) or (12-IVa) as defined supra.

The present invention also concerns an environmentally-friendly stabiliser, which produces no mutagenic or carcinogenic by-products for stabilising a nitrate ester-based propellant comprising nitrocellulose. The said carcinogenic-free stabiliser being in the form of a mixture comprising: (a) a non-aromatic compound of formula (12) as defined supra and (b) an aromatic compound as complementary stabiliser. Any of the aromatic compounds (13) to (18) defined above can be used as complementary stabiliser.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

As illustrated in FIG. 1, degradation of nitrocellulose forms free oxide radicals 2 (R—O) and NOx. These degradation products are capable of reacting further and with nitrocellulose 1, which can rapidly lead to an explosion of the nitrate ester-based propellant due to excess heat generation. The most commonly used stabilisers are certainly akardite (AkII) 4 and diphenyl amine (DPA) 5 as illustrated in FIG. 2(a). Akardite (AkII) 4 when exposed to NOx, forms carcinogenic N—NO compounds 6 as illustrated in reaction (A) of FIG. 2(a). Simultaneously or sequentially, it dissociates upon exposure to heat to form diphenyl amine (DPA) 5 following reaction (B) of FIG. 2(a). Whether used directly as a stabiliser, or present in the composition following heat dissociation (B) of akardite 4, diphenyl amine (DPA) 5 stabilises a propellant composition by the following mechanism. A free radical alkoxy group generated by the propellant abstracts the hydrogen of the amine group of DPA 5 to form a stable compound (ROH, 9) (cf. reaction (C) of FIG. 2(a)). The radical formed on the amine 8 can react with a NOx to form stable N-nitrosodiphenylamine 10 (cf. reaction (D) of FIG. 2(a)). The NNO group of N-nitrosodiphenylamine 10 is, however, carcinogenic and should be avoided for safety reasons. Triphenylamine has been tested in the past in order to prevent formation of NNO groups, but with little success in stabilisation properties. Hindered phenols as illustrated in FIG. 2(b) effectively react with free oxide radicals (R—O) but forming stable components which are unlikely to further react with NOx (cf. reaction ① of FIG. 2(b)). The efficiency of such stabilisers is limited to short periods of time only because of rapid phenols depletion.

A non-aromatic compound 12 comprised in a stabiliser as used in the present invention has a general formula (12-I), (12-II), (12-III) or (12-IV):

(12-III)

(12-IV)

wherein R¹ represents a ketone, hydroxyl, carboxyl, aldehyde or (un)saturated alkyl group.

The non-aromatic compound of formula (12-I) is preferably alpha ionone 12-Ia, wherein R¹ is —C(O)CH₃:

12-Ia

The R¹ group of the non-aromatic compound of formula (12-IV) is preferably:

In a preferred embodiment, the stabiliser corresponds to pseudo ionone.

Not wishing to be bound by any theory, it is believed that a stabiliser 12, as defined in the present invention contains a very labile proton which can react with radical alkoxy groups 2 and NOx species (FIG. 1) formed by degradation of the nitrate ester 1. Successive by-products are likely formed, and are also capable of reacting with NOx and alkoxy radicals from the degradation of the nitrate ester 1, increasing the efficiency of stabiliser function. Since no harmful NNO groups are formed due to the lack of nitrogen atoms in the-non-aromatic compound 12 structure, the stabiliser according to the present invention produces little to no carcinogenic and mutagenic by-products.

Figure 5:
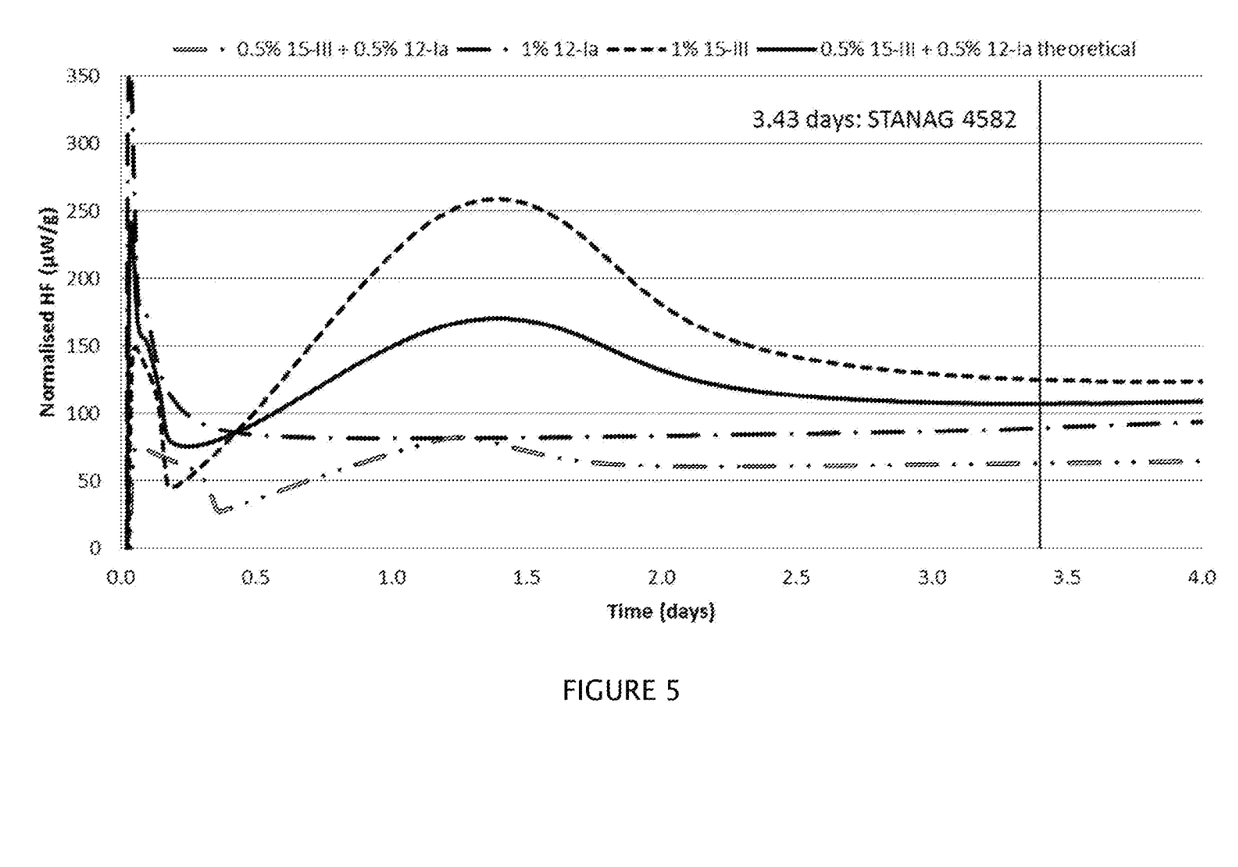
FIG. 5 shows the normalised heat flows expressed in μW/g generated by propellant compositions stabilised with 1 wt. % of the non-aromatic compound (alpha ionone 12-Ia) alone (mixed line), 1 wt. % of the aromatic compound (eugenol 15-III) alone (dashed line), the combination of 0.5 wt. % of 12-Ia with 0.5 wt. % of a complementary stabiliser 15-III as actual value (double dotted mixed line), and the combination of 0.5 wt. % of 12-Ia with 0.5 wt. % of complementary stabiliser 15-III as theoretical value for a zero synergy effect (solid line).
Figure 6:
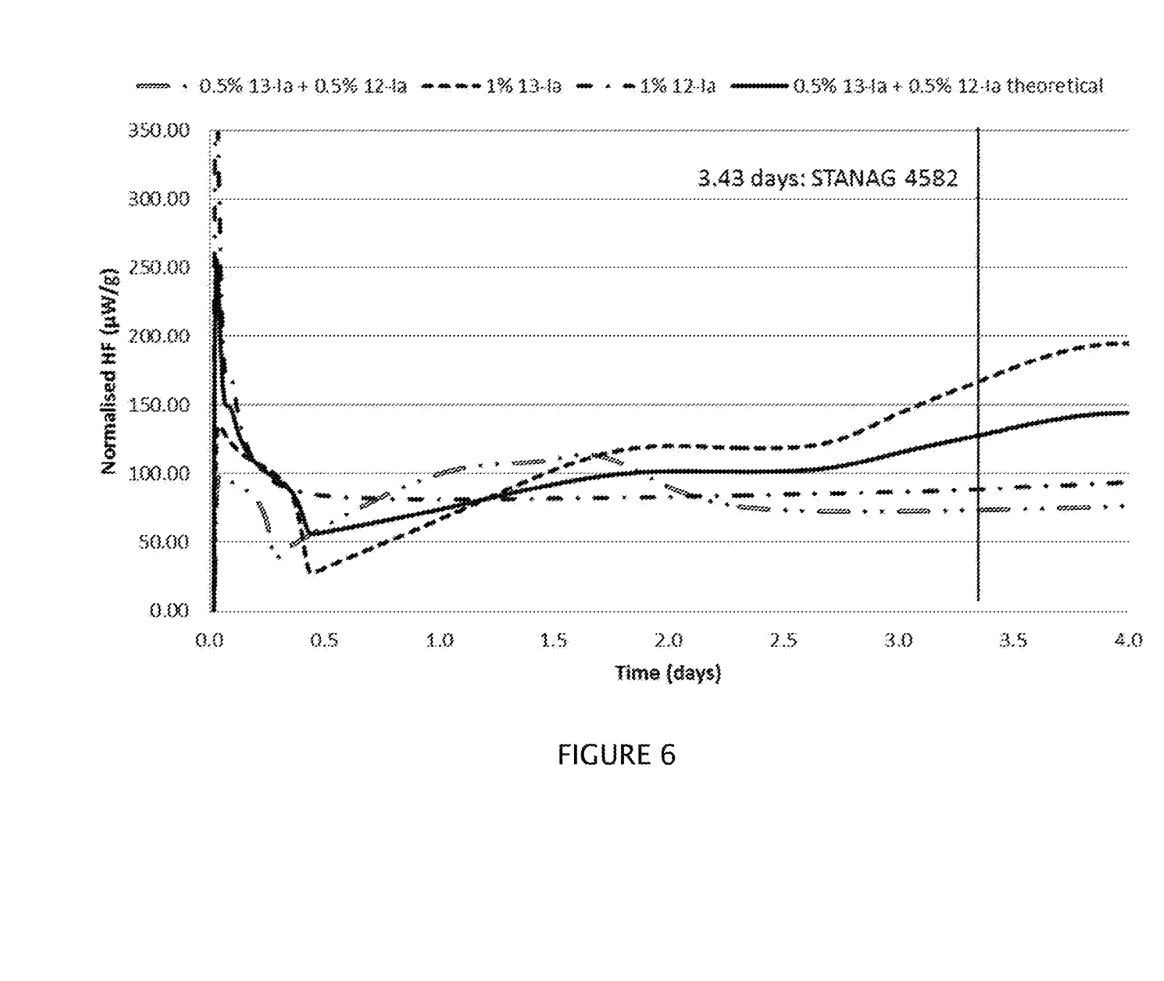
FIG. 6 shows the normalised heat flows expressed in μW/g generated by propellant compositions stabilised with 1 wt. % of the non-aromatic compound (alpha ionone 12-Ia) alone (mixed line), 1 wt. % of the aromatic compound (2,3,5-trimethylphenol, 13-Ia) alone (dashed line), the combination of 0.5 wt. % of 12-Ia with 0.5 wt. % of a complementary stabiliser 13-Ia as actual value (double dotted mixed line), and the combination of 0.5 wt. % of 12-Ia with 0.5 wt. % of complementary stabiliser 13-Ia as theoretical value for a zero synergy effect (solid line).

It has been observed that even better stabilisation was obtained when combining a non-aromatic compound of formula (12) with an aromatic compound as complementary stabiliser yielding a synergistic effect on stabilisation as illustrated in FIGS. 5 and 6 by comparing the actual values (double dotted mixed lines) measured on a nitrocellulose composition stabilised with such combination with the theoretical values (solid lines) of the heat flows calculated by averaging the effects of each compound individually.

For example, a substituted phenol compound (13) can be used as a complementary stabiliser producing little to no carcinogenic and mutagenic by-products in the present invention together with the non-aromatic compound (12). Said complementary stabiliser can also be used instead of, rather than together with the non-aromatic compound (12), but the combination of a non-aromatic component (12) with a substituted phenol compound (13) yielded enhanced stabilisation. Said phenol compound has the following general formula (13-I):

(13-I)

Wherein R³ represents: (i) H, (ii) alkyl substituted or not, or (iii) an alkoxy group, preferably not an aromatic group bound to the phenol through a ketone; and R⁴ and R⁵ are same or different, and represent (i) alkyl substituted or not, or (ii) alkoxy group. In a preferred embodiment, R³ represents CH₃. Again, R⁴ and R⁵ can be same, and preferably represent CH₃, yielding a complementary stabiliser of formula (13-Ia):

(13-Ia)

In another embodiment, R³ represents H. R⁴ and R⁵ are then preferably same. R⁴ and R⁵ can be alkyls, in particular tert-C₄H₉. Alternatively, R⁴ and R⁵ can be an alkoxy group, advantageously, methoxy, yielding a complementary stabiliser of formula (13-Ib):

(13-Ib)

Alternatively, R⁴ and R⁵ may represent tert-C₄H₉.

In an alternative embodiment, a trialkoxy benzene (14) can also be used as complementary stabiliser producing little to no carcinogenic and mutagenic by-product in the present invention. Said trialkoxy benzene 14 has the following general formulae (14-I) or (14-II):

(14-I)

(14-II)

Wherein R⁶, R⁷ and R⁸ are same or different and represent $C_{1-5}$ alkyl unsubstituted or substituted with an alkoxy group.

$R^6$ and $R^8$ in formulae (14-I) or (14-II) preferably represent $CH_3$. More preferably, $R^7$ represents one of:

·CH₃ a polymeric alkoxylated chain, preferably endcapped with a benzene of formula (14-I) of the type, wherein n is comprised between 1 and 20, preferably between 3 and 10.

In an alternative embodiment, an aromatic compound (15) having a general formula (15-I) can be also used as a complementary stabiliser together with a non-aromatic compound (12) in the present invention or, alternatively, on its own, (15-I)

Wherein:
$R^9$ represents, alkyl substituted or not;
$R^{10}$ represents
 (i) H;
 (ii) unsaturated alkyl group;

(iii)

(iv)

(v)

$R^{11}$ represents, H, alkyl substituted or not, or $OR^{15}$;
$R^{12}$ represents, alkyl substituted or not, aromatic ring substituted or not, or $OR^{15}$;
$R^{13}$ represents, alkyl substituted or not, aromatic ring substituted or not, or $OR^{16}$;
$R^{14}$ represents, aromatic ring substituted or not;
$R^{15}$ represents, alkyl substituted or not, or aromatic ring substituted;
$R^{16}$ represents, alkyl substituted or not, or aromatic ring substituted

In a preferred embodiment, $R^9$ represents $C_{1-5}$ alkyl substituted or not, preferably $CH_3$;
Further, it is preferred that $R^{17}$ represents:

(i)

(ii)

(iii)

or (iv)

wherein $R^{17}$ represents H, alkyl substituted or not, or aromatic ring substituted or not. For example, eugenol (15-III) or isoeugenol (15-IV) are suitable complementary stabilisers according to the present invention.

(15-III)

(15-IV)

A more preferred embodiment of composition according to the present invention comprises a curcumin derivative of formula (15-II) as stabiliser, (15-II)

Wherein R$^9$ and R$^{18}$ are same or different and represent alkyl substituted or not, preferably C$_{1-5}$, more preferably CH$_3$; R$^{11}$ and R$^{19}$ are same or different and represent H or alkyl substituted or not (e.g., C$_{1-5}$ alkyl), wherein each of R$^9$ and R$^{18}$, and R$^{11}$ and R$^{19}$, are preferably same, and more preferably both are H.

In another alternative embodiment, a substituted phenol compound (16) having the general formula (16-I) can also be used as a complementary stabiliser:

(16-I)

wherein: R$^{20}$, R$^{21}$ and R$^{22}$ are the same or different and represent: (i) alkyl-substituted or not, (ii) alkoxy group.

In another alternative embodiment, a substituted phenol compound (17) having the general formula (17-I) can also be used as a complementary stabiliser:

(17-I)

wherein: R$^{23}$, R$^{24}$, R$^{25}$ and R$^{26}$ are the same or different and represent: (i) alkyl-substituted or not, (ii) alkoxy group.

In another alternative embodiment, a tocopherol-class compound (18) with the general formula (18-I) can also be used as a complementary stabiliser:

(18-1)

wherein:
X is oxygen or nitrogen;
R$^{27}$ is selected from the group consisting of hydrogen, alkyl, alkenyl, alkynyl, aryl, heteroaryl, carboxylic acid, carboxylate, ester, saccharide, alkoxy-linked saccharide, alcohol, and ether;
R$^{28}$ is selected from the group consisting of hydrogen methyl, benzyl carboxylic acid, benzyl carboxylate, benzylester, and saccharide;
R$^{29}$ is selected from the group consisting of hydrogen, methyl, benzyl carboxylic acid, benzyl carboxylate, benzylester and, saccharide;
R$^{30}$ is selected from the group consisting of methyl, benzyl carboxylic acid, benzyl carboxylate, benzylester, and saccharide;
R$^{31}$ is selected from the group consisting of alkyl and alkenyl;
Wherein when X is nitrogen, said nitrogen is substituted with R$^{32}$, wherein R$^{32}$ is selected from the group consisting of hydrogen and methyl.

Surprisingly a stabiliser comprising the non-aromatic compound 12 and a complementary stabiliser comprising an aromatic selected from one or more of a substituted phenol compound (13, 16 or 17), a trialkoxy benzene (14), an aromatic compound (15) or a tocopherol species (18) provides a synergic stabilising effect. For example, FIG. 5 shows the positive synergic effect when stabiliser 12-Ia is used with compound 15-III. The total heat release is less for the combination of the two molecules (cf. double dotted mixed line), than for the averaged sum of the individual heat releases for each stabiliser (cf. solid line). FIG. 6 is another example of a positive synergic effect for the combination of molecules 12-Ia and 13-Ia (compare actual (double dotted mixed line) and theoretical (solid line) values of heat flow, showing a significantly lower heat flow after two days testing.

Figure 3A:
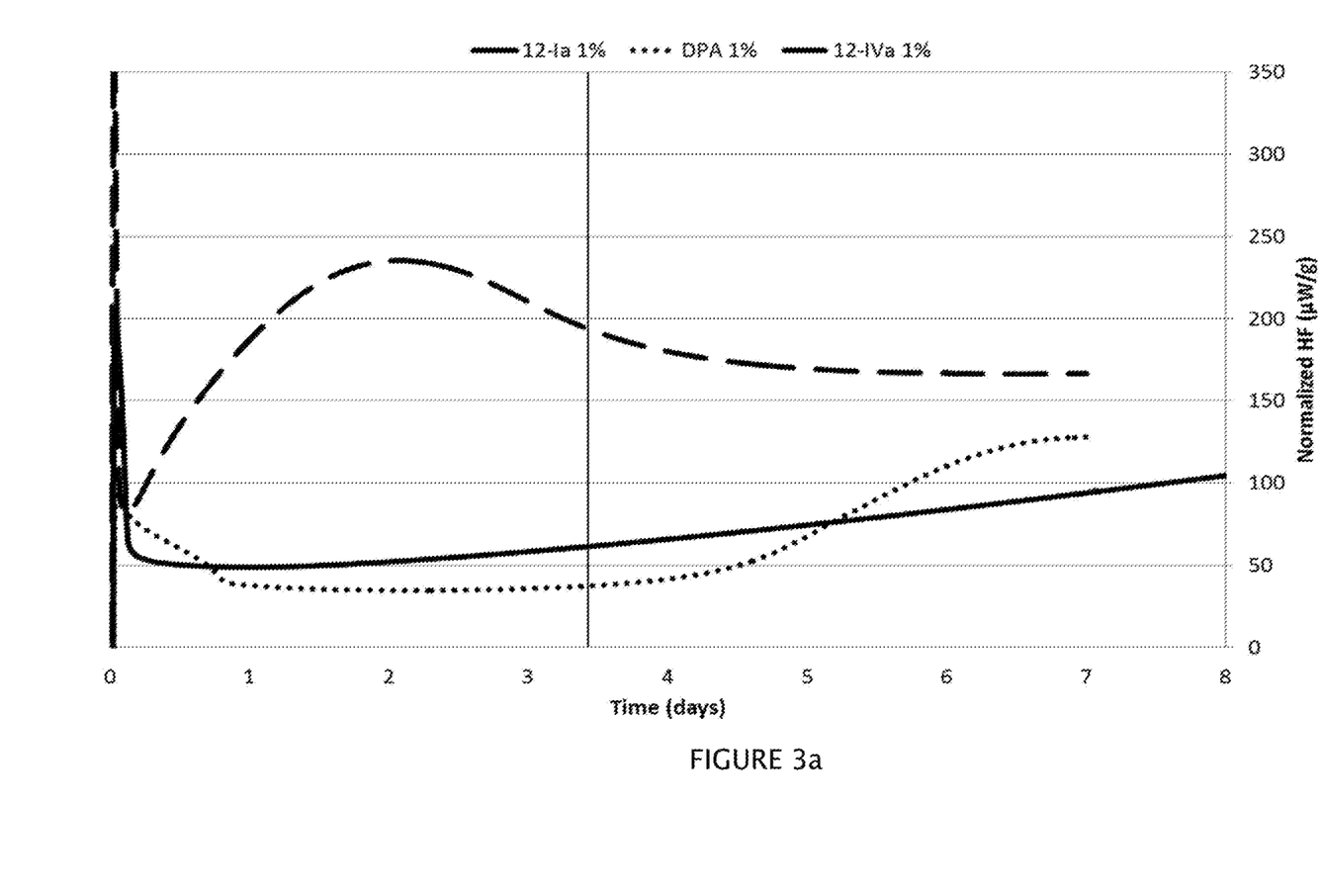
FIGS. 3(a) to 3(c) show the normalised heat flow expressed in μW/g generated by propellant compositions stabilised with diphenylamine (DPA) as conventional stabiliser or a stabiliser comprising a non-aromatic compound consisting of formulae (12-Ia) and (12-IVa) for (a) single base nitrocellulose propellants; (b) double base nitrocellulose/nitroglycerine (80/20 wt. %) propellants and (c) double base nitrocellulose/nitroglycerine (60/40 wt. %) propellants.
Figure 3B:
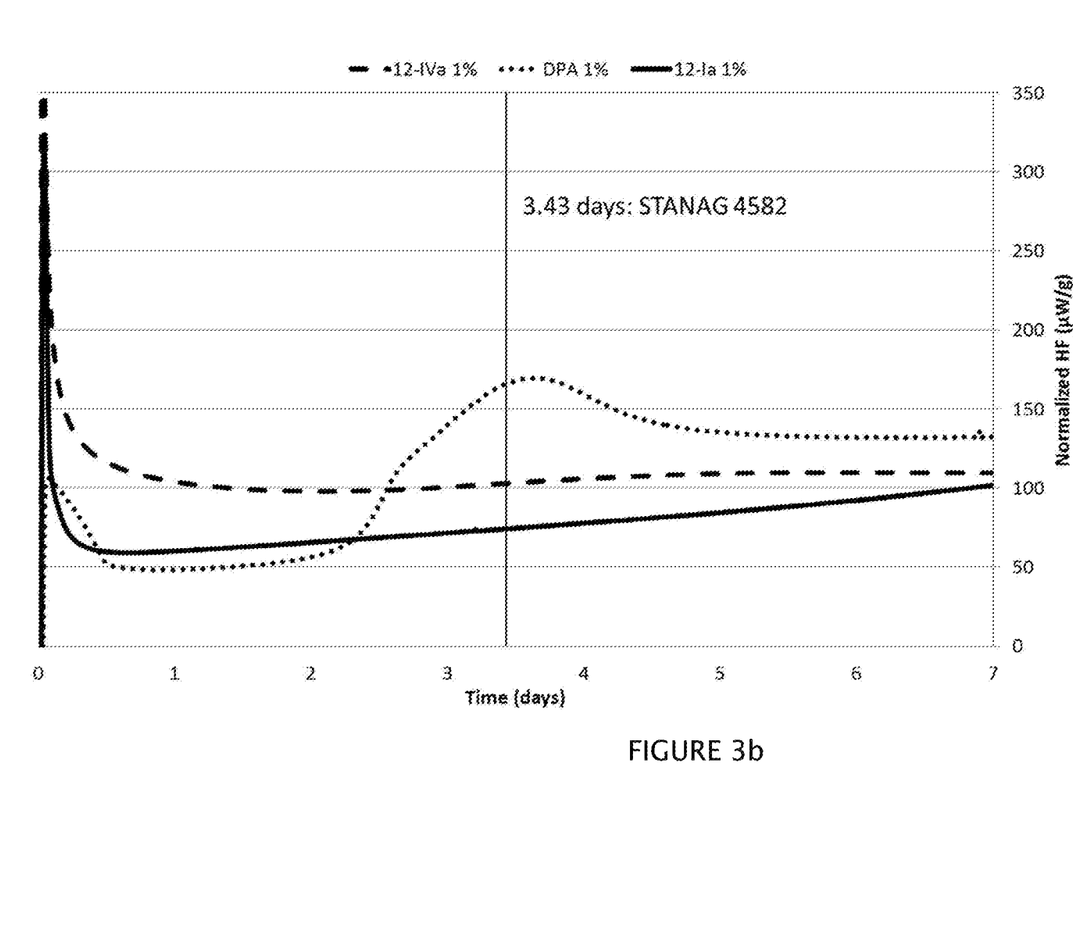
Figure 3C:
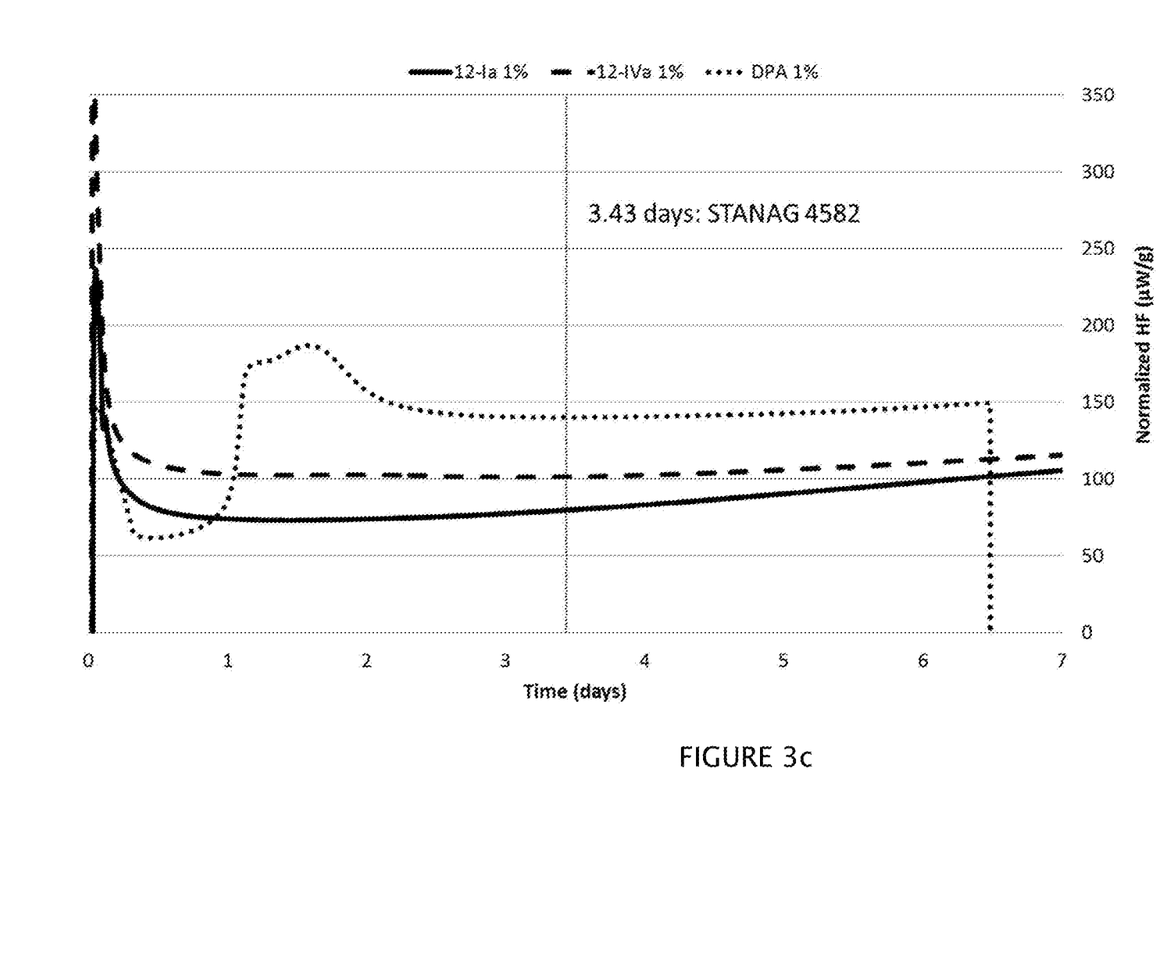

The propellant composition of the present invention may be a single base propellant, wherein the nitrate ester propellant consists of nitrocellulose only or a double base propellant, wherein nitrocellulose is combined with a blasting oil and/or at least one energetic additive. The most common blasting oil is nitroglycerine. FIG. 3(a) compares the stability of a single base propellant composition stabilised with 1 wt. % of DPA 5 as conventional stabiliser of the prior art with a stabiliser comprising 1 wt. % of a non-aromatic compound 12 consisting of formula 12-Ia and 12-IVa-according to the present invention. FIG. 3(b) illustrates the same for a double base propellant composition wherein the nitrate ester propellant comprises 80 wt. % nitrocellulose and 20 wt. % nitroglycerine. FIG. 3(c) compares the stability of a 60 wt. % nitrocellulose and 40 wt. % nitroglycerine double base propellant composition stabilised with 1 wt. % of DPA 5 as conventional stabiliser of the prior art, 1% of the non-aromatic compound 12-Ia and 1% of 12-IVa. Nitroglycerine is a commonly used blasting oil. Energetic additives, on the other hand, can be an energetic plasticiser selected from the group of nitramines such as butyl-NENA, dinitrodiazaalkane (DNDA), or an explosive such as RDX, HMX, FOX7, FOX12, CL20. A double base propellant composition according to the present invention preferably comprises a nitrate ester-based propellant comprising not more than 60 wt. % blasting oil (such as nitroglycerine) or energetic additive with respect to the total weight of nitrate ester based propellant. More preferably, it comprises between 5 and 45 wt. %, most preferably between 7 and 22 wt. % blasting oil or energy additive, with respect of the total weight of nitrate ester-based propellant. A most preferred blasting oil is nitroglycerine.

A propellant composition according to the present invention comprises a stabiliser comprising a non-aromatic compound (12), for example consisting of formula (12-I), preferably in an amount comprised between 0.1 and 5.0 wt. %, more preferably between 0.2 and 2.0 wt. %, most preferably between 0.5 and 1.5 wt. %, with respect to the total weight of the composition.

Unless otherwise specified, the expression "substituted or not" is to be construed as any —H in a molecule may be substituted by any of an alkyl, alkene, or an aromatic ring. A propellant composition is considered as being a "nitrocellulose-based propellant composition" if it comprises at least 40 wt. % nitrocellulose, based on the total weight of the composition.

Beside a nitrate ester based propellant and a stabiliser, a propellant composition according to the present invention may comprise additives. In particular, it may comprise one or more of the following additives:
(a) a potassium salt, such as potassium nitrate ($KNO_3$) or sulphate ($K_2SO_4$), preferably in an amount comprised between 0.01 and 1.5 wt. %;
(b) combustion moderators such as phthalates, centralite or citrate derivatives, preferably in an amount comprised between 0.5 and 10.0 wt. %;
(c) an anti-static agent such as graphite, preferably in an amount comprised between 0.01 and 0.5 wt. %; and
(d) calcium carbonate, preferably in an amount comprised between 0.01 and 0.7 wt. %, Wherein the wt. % are expressed in terms of the total weight of the propellant composition.

An example of propellant composition according to the present invention is listed in Table 1.

TABLE 1 typical propellant compositions according to the present invention

| component | single base wt. % | double base wt. % |
|---|---|---|
| nitrocellulose | 89.0-96.0 | 82.0-86.0 |
| nitroglycerine | 0.0 | 7.0-11.0 |
| $KNO_3$ | 0.5-1.0 | 0.5-1.0 |
| dibutylphthalate | 3.0-7.0 | 3.0-7.0 |
| graphite | 0.2-0.4 | 0.2-0.4 |
| calcium carbonate | <0.7 | <0.7 |
| stabiliser of formula (12) | 0.15-2.0 | 0.15-2.0 |

Experimental Tests

STANAG 4582 (Ed. 1) of Mar. 9, 2007 entitled "Explosives, nitrocellulose based propellants, stability test procedure and requirements using heat flow calorimetry", defines an accelerated stability test procedure for single-, double-, and triple base propellants using heat flow calorimetry (HFC). The test is based on the measurement of the heat generated by a propellant composition at a high temperature. Fulfillment of the STANAG 4582 (Ed.1) test qualifies a propellant composition for a 10 year stability at 25° C.

A sample of propellant composition is enclosed in a hermetically sealed vial and positioned in a heat flow calorimeter having a measuring range corresponding to 10 to 500 μW/g. The sample is heated and maintained at a constant temperature of 90° C. for the whole duration of the test and the heat flow is measured and recorded. A heat flow not exceeding 350 μW/g for a period of 3.43 days at 90° C. is considered to be equivalent to at least 10 years of safe storage at 25° C. The graphs of FIGS. 3 to 6 show the stability of a composition as a function of time measured as defined above. The full scale of the ordinate (normalised heat flow) corresponds to a value of 350 μW/g not to be exceeded according to STANAG 4582 (Ed.1), and the vertical straight line indicates 3.43 days. The initial heat flow peak of the graphs of FIGS. 3 to 6 is ignored as it is not representative of any specific reaction or phase transformation of the propellant composition, provided it does not exceed an exotherm of 5 J.

FIGS. 3(a), (b) and (c) show the results of the stability tests carried out on a single- and double-base nitrocellulose based propellants, the latter comprising 40 wt. % nitroglycerine, for DPA 5 as prior art stabiliser and stabilisers comprising a non-aromatic compound (12-Ia) or (12-IVa), in amounts of 1 wt. %, with respect to total weight of the propellant composition. The results for the stabilisers comprising component (12-Ia) and (12-Iva) according to the present invention are shown by a solid line and a long dashed line, respectively, and those for diphenyl amine (DPA) of the prior art are shown by a dotted line. The heat flow never exceeds 100 μW/g for 3.43 days with non-aromatic compounds (12-Ia and 12-IVa), when STANAG 4582 (Ed.1) requires to maintain the heat flow below 350 μW/g (full scale of the ordinate) as shown in FIG. 3(c). The tests on single base propellants were carried out for a longer period, showing a prolonged stability of the compositions with a heat flow continuously lower than 250 μW/g for up to 8 days (which corresponds to a stability of more than 25 years at normal storage conditions. It can be seen that both stabilisers according to the present invention as well as DPA according to prior art fulfil the requirements of STANAG 4582 (Ed.1).

Stabilisers comprising a non-aromatic component such as 12-Ia and 12-IVa according to the present invention are advantageous over conventional stabilisers (i.e. DPA 5 and AKII 4) because, (a) Contrary to DPA and Akardite, stabilisers according to the present invention do not generate any N—NO carcinogenic by-product upon their stabilisation activity.

(b) DPA curve (dotted line) for double based propellant in FIGS. 3(b) and 3(c) shows a sharp peak stabilising in a plateau at higher heat flow values, suggesting that all DPA was spent after only about two days (cf. reactions (C) and (D) in FIG. 2(a)) whence stabilisation probably proceeds by reactions with by-products. By contrast, no discontinuity in the heat flow can be identified with stabilisers comprising 12-Ia or 12-IVa over 3.5 days and even for over 7 days, as revealed in FIGS. 3(b) and 3(c).

(c) As revealed in FIG. 3(a) discussed supra with respect to single base nitrocellulose propellants, the stabilisers of the present invention allow the maintenance of a heat flow substantially lower than 350 μW/g at a temperature of 90° C. for periods up to 8 days. Longer term tests with DPA, however, are not easily performed because vials containing a composition stabilised with DPA leaked (FIG. 3c), as shown by the sudden drop in the curve appearing earlier than the ones stabilised according to the present invention. It is assumed that gas generation by the reactions with DPA raises the pressure inside the vials above their limit of resistance, leading to the bursting open of the vials after a few days testing. Uncontrolled pressure rises must be avoided during transportation or storage of propellant compositions for obvious reasons.

Figure 4:
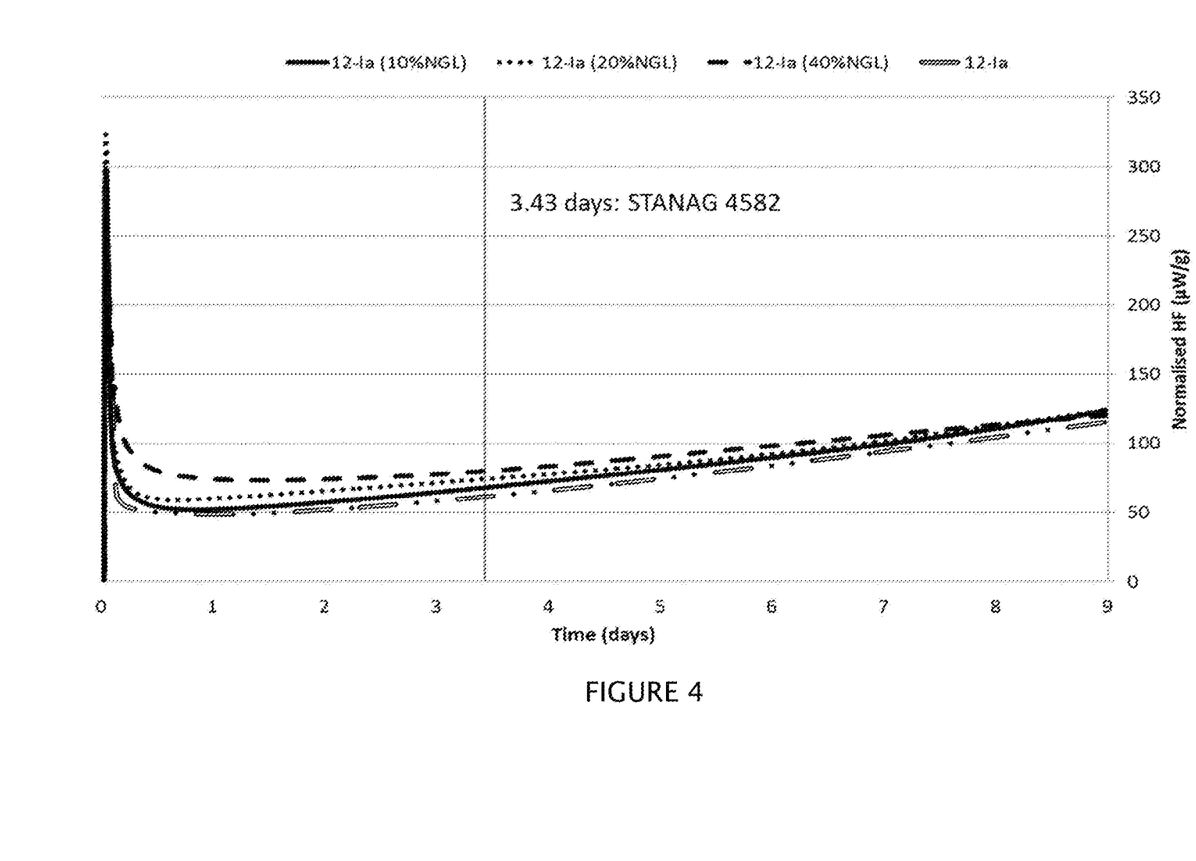
FIG. 4 shows the normalised total heat flows expressed in μW/g generated by propellant compositions stabilised with a stabiliser comprising the non-aromatic compound of formula (12-Ia) for double base nitrocellulose/nitroglycerine (90/20 wt. %) propellants, double base nitrocellulose/nitroglycerine (80/20 wt. %) propellants and double base nitrocellulose/nitroglycerine (60/40 wt. %) propellants according to the present invention. This figure shows the stabilisation effect of alpha ionone (12-Ia). on double-base nitrocellulose-based propellant compositions as a function of the amount of nitroglycerine in the compositions.

FIG. 4 shows the results of the stability tests carried out on a double-base nitrocellulose based propellants, comprising 10, 20 and 40 wt. % nitroglycerine, each composition comprising the non-aromatic compound 12-Ia in an amount of 1 wt. %, with respect to the total weight of the propellant composition.

FIG. 5 shows the normalised heat flows expressed in μW/g generated by propellant compositions stabilised with:
- 1 wt. % of the non-aromatic compound (alpha ionone 12-Ia) alone (mixed line) according to the present invention,
- 1 wt. % of the aromatic compound (eugenol 15-III) alone (dashed line), not according to the present invention,
- the combination of 0.5 wt. % of stabiliser 12-Ia with 0.5 wt. % of complementary stabiliser 15-III (double dotted mixed line), according to the present invention as actually measured on a sample, and
- the theoretical combination of 0.5 wt. % of stabiliser 12-Ia with 0.5 wt. % of complementary stabiliser 15-III (solid line), calculated by averaging the individual contribution of each component thus ignoring any synergy effect.

It can be seen that the two best stabiliser compositions are the ones according to the present invention, namely, a non-aromatic compound of formula 12-Ia used alone or in combination with a complementary stabiliser of formula 15-III.

FIG. 6 shows the normalised heat flows expressed in μW/g generated by propellant compositions stabilised with:
- 1 wt. % of the non-aromatic compound (alpha ionone 12-Ia) alone (mixed line) according to the present invention,
- 1 wt. % of the aromatic compound (2,3,5-trimethylphenol, 13-Ia) alone (dashed line), not according to the present invention,
- the combination of 0.5 wt. % of 12-Ia with 0.5 wt. % of a complementary stabiliser 13-Ia as actual value (double dotted mixed line), according to the present invention as actually measured on a sample, and
- the theoretical combination of 0.5 wt. % of stabiliser 12-Ia with 0.5 wt. % of complementary stabiliser 13-Ia (solid line), calculated by averaging the individual contribution of each component thus ignoring any synergy effect.

The propellant compositions of the present invention mark the beginning of the use of a new generation of stabilisers which can be referred to as "green or environmentally-friendly stabilisers," which combine efficient, long term stability of nitrocellulose-based propellants without formation of any detectable amounts of carcinogenic or mutagenic by-products.

The invention claimed is:

1. A nitrocellulose-based propellant composition comprising:
   (a) a nitrate ester-based propellant comprising nitrocellulose; and
   (b) a stabiliser comprising a non-aromatic compound consisting of a general ionone formula (12-I), (12-II), (12-III) or (12-IV):

(12-I)

(12-II)

(12-III)

(12-IV)

wherein $R^1$ represents a ketone, hydroxyl, carboxyl, aldehyde, an (un)saturated alkyl group or —C(O)CH$_3$.

2. The propellant composition according to claim 1, wherein the nitrate ester-based propellant consists of nitrocellulose alone as a single base or of a mixture comprising nitrocellulose in combination with at least a blasting oil and/or at least one energetic additive as a double or higher base.

3. The propellant composition according to claim 1, wherein the non-aromatic compound is a substance capable of reacting by H-abstraction with radical groups formed by degradation of the nitrate ester to form a first by-product capable of further reacting with NOx and/or alkoxy groups formed by degradation of the nitrate ester to form a second by-product comprising no NNO groups.

4. The propellant composition according to claim 3, wherein the second by-product is capable of reaction with radical groups formed by degradation of the nitrate ester for forming third and subsequent by-products capable of reacting with such radical alkoxy groups or with NOx.

5. The propellant composition according to claim 2, wherein the blasting oil comprises at least a nitrated polyol obtainable by nitration of polyol selected from a group consisting of glycerol, glycol, diethylene glycol, triethylene glycol and metriol, and wherein the at least one energetic additive is an energetic plasticizer selected from the group of nitramines, including butyl-NENA, dinitrodiazaalkane (DNDA), or is an explosive comprising RDX, HMX, FOX-7, FOX-12, CL20.

6. The propellant composition according to claim 1, wherein $R^1$ represents one of:
acetyl ketone —C(O)CH$_3$; or
a component of formula wherein $R^2$ represents CH$_2$OH, —CHO, or, —CH$_2$OC(=O)R$^3$, R$^3$ represents alkyl group substituted or not, and
wherein said non-aromatic compound is retinyl palmitate.

7. The propellant composition according to claim 1, wherein the non-aromatic compound is present in the composition in an amount comprised between 0.1 and 5.0 wt. %, with respect to the total weight of the composition.

8. The propellant composition according to claim 1, further comprising an aromatic compound as complementary stabiliser.

9. The propellant composition according to claim 1, wherein the nitrate ester based propellant comprises not more than 60 wt. % nitroglycerine, with respect of the total weight of nitrate ester based propellant.

10. A method comprising:
stabilising a nitrate ester based propellant comprising nitrocellulose with a non-aromatic component of a general formula (12-I), (12-II), (12-III) or (12-IV):

(12-I)

(12-II)

(12-III)

(12-IV)

wherein:

$R^1$ represents ketone, hydroxyl, aldehyde, carboxyl or unsaturated alkyl group.

11. The propellant composition according to claim 7, wherein the non-aromatic compound is present in the composition in an amount comprised between 0.2 and 2.0 wt. %, with respect to the total weight of the composition.

12. The propellant composition according to claim 11, wherein the non-aromatic compound is present in the composition in an amount comprised between 0.5 and 1.0 wt. %, with respect to the total weight of the composition.

13. The propellant composition according to claim 9, wherein the nitrate ester based propellant comprises between 5 and 45 wt. %, with respect of the total weight of nitrate ester based propellant.

14. The propellant composition according to claim 13, wherein the nitrate ester based propellant comprises between 7 and 22 wt. % nitroglycerine, with respect of the total weight of nitrate ester based propellant.

* * * * *